Sept. 19, 1939. J. GAUJARD Plant Pat. 338
ROSE PLANT
Filed Jan. 20, 1939
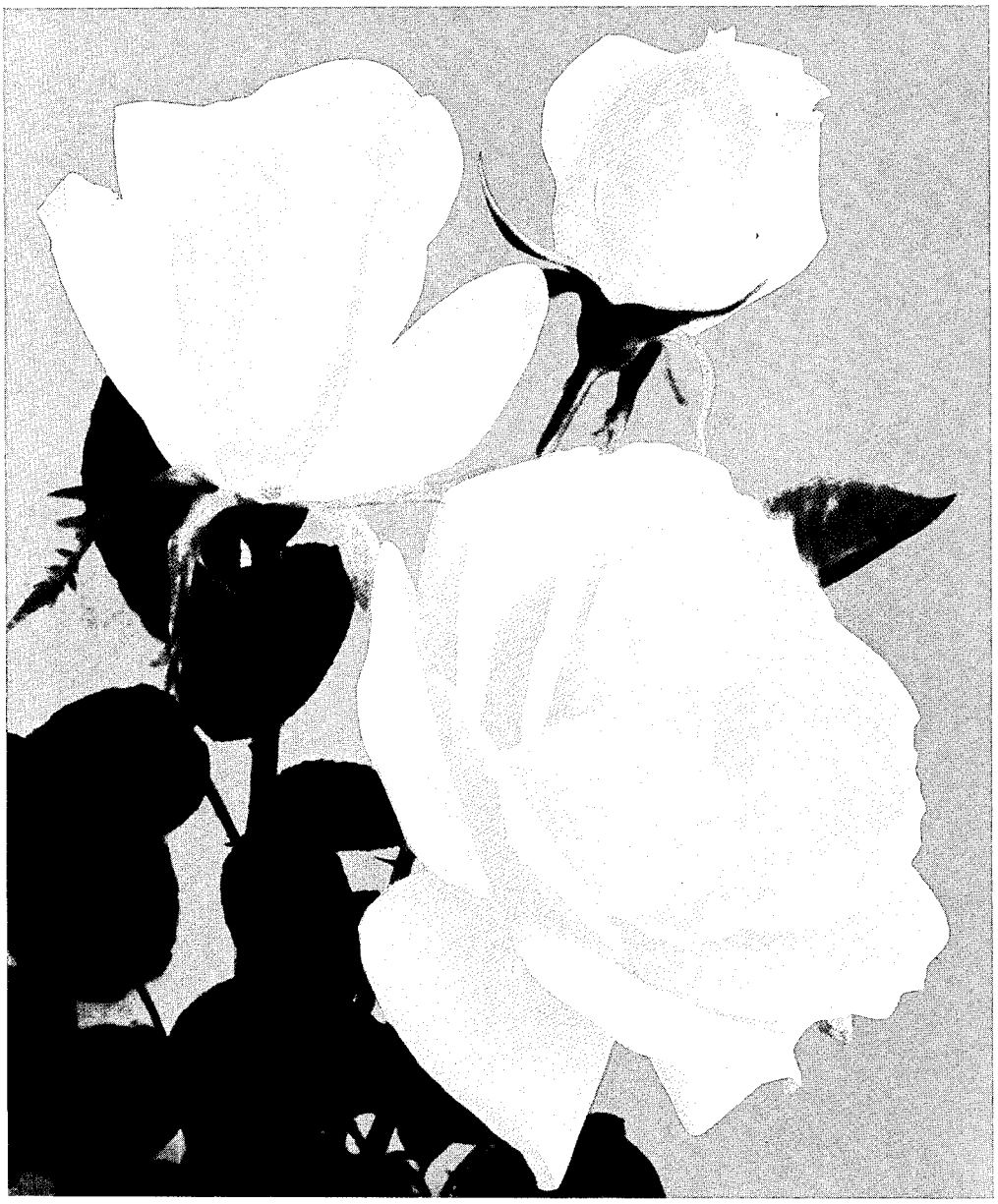
Inventor
Jean Gaujard
By Robb & Robb
Attorneys Patented Sept. 19, 1939

Plant Pat. 338

UNITED STATES PATENT OFFICE

338

ROSE PLANT

Jean Gaujard, Feyzin, France, assignor to Jackson & Perkins Company, Newark, N. Y.

Application January 20, 1939, Serial No. 252,029

1 Claim. (Cl. 47—61)

The present invention relates to a new and distinct variety of Hybrid Tea rose, a seedling of Julien Potin crossed with an unnamed seedling.

This new variety is distinguished from other similar roses by the combination of colors of the inside and reverse side of the petals and the excellent form of the buds and flowers, all of which give to it an aristocratic richness not heretofore found.

Of equal or greater importance is the habit of vigorous upright growth, not usually found in connection with plants of the peculiar coloring of the blooms.

A further valuable difference is the disease resistance of the plant.

This new rose has been asexually reproduced and found to come true to form.

The following is a detail description of the new variety, the color designations being in accord with Ridgeway's Color Chart:—

Parentage:
- *Seed parent.*—Julien Potin.
- *Pollen parent.*—Unnamed seedling.

Classification:
- *Botanic.*—Hybrid Tea.
- *Commercial.*—Hybrid Tea.

*Flower*

Blooming habit:
- Observations made in the morning of June 26, 1938, at Newark, New York.
- Recurrent-intermittent.

Bud:
- *Size.*—Large.
- *Form.*—Long, pointed. Unaffected by wet or hot weather.
- *Color.*—When sepals first divide—Plate 13, Old Rose. When petals begin to unfurl—Plate 13, Old Rose. When half blown: inside of petals—Plate 4, Buff Yellow; reverse of petals—Plate 13, Jasper Pink.
- *Sepals.*—Serrated, branched, curl back.
- *Calyx.*—Shape—funnel. Size—broad. Aspect—smooth.
- *Peduncle.*—Length—long. Aspect—prickly. Color—Plate 27, Corinthian Red. Strength—stiff, heavy.
- *Opening.*—Bud opens well.

Bloom:
- *Size.*—Very large. Average size when fully expanded—6 inches.
- *Borne.*—Singly.
- *Stems.*—Long, strong.
- *Form.*—When first open, high center. Permanence—retains its form to the end.
- *Petalage.*—Double (full but open center). Number of petals under normal conditions—45.
- *Color.*—Center of flower—Plate 3, Light Orange Yellow. Outer petals—Plate 4, Buff Yellow. Base of petals (aiglet)—Plate 16, Strontian Yellow. Inside of petals—Plate 4, Maize Yellow. Reverse of petals—Plate 13, Alizarine Pink.
- *Variegations.*—None.
- *Discoloration.*—None.

Petals:
- *Texture.*—Thick, soft. Is affected by wet weather—sometimes balls.
- *Appearance.*—Inside—satiny. Outside—shiny.
- *Form.*—Oval, pointed.
- *Arrangement.*—Irregular. Petaloids in center—few, small.
- *Persistence.*—Drop off cleanly.
- *Fragrance.*—Slightly. Nature—"Old Rose" perfume (Centifolia).
- *Lasting quality on the plant and as cut flowers.*—Long.

Genital organs:
- *Stamens, anthers.*—Medium, many. Color—Plate 4, Apricot Yellow. Arrangement—regular round styles.
- *Stamens, filaments (threads).*—Medium length. Color—Plate 2, Grenadine.
- *Pollen.*—Plate 3, Raw Sienna.
- *Styles.*—Columnar, bunched—medium length, heavy.
- *Stigmas.*—Plate 3, Light Orange Yellow.
- *Ovaries.*—Some protruding from calyx.

Fruit:
- Variety is fertile with its own pollen.
- *Form.*—Ovoid, flat headed.
- *Aspect.*—Smooth.
- *Sepals.*—Permanent; recurved.

*Plant*

Form:
- Bush.

Growth:
- Vigorous, upright.

Foliage:
- Five-seven leaflets.
- *Size.*—Medium.
- *Quantity.*—Normal.
- *Color.*—New foliage: upper side—Plate 4, Olive Green; edges and ribs—Plate 13, Hessian Brown; under side—Plate 13, Hay's Maroon. Old foliage: upper side—Plate 31, Dark Cress Green; under side—Plate 31, Rainette Green. Shape—oval pointed.
- *Texture.*—Upper side—smooth. Under side—smooth. Ribs and veins—ordinary.
- *Edge.*—Serrated (saw toothed).
- *Serration.*—Single, small.
- *Rachis.*—Color—Plate 31, Chrysolite Green. Under side—prickles.
- *Stipules.*—Short, bearded.
- *Disease resistance.*—Resistant, immune.

Wood:

*New wood.*—Color—Plate 13, Hay's Maroon. Bark—smooth.

*Old wood.*—Color—Plate 31, Light Cress Green. Bark—rough.

Thorns (divided into thorns, prickles and short needles):

*Thorns.*—Quantity: on main stalks from base—many; on laterals from stalk—many. Form—flat base, medium, hooked downward. Color when young—Plate 13, Van Dyke Red. Position—irregular.

*Prickles.*—Quantity: on main stalks—many; on laterals—few. Color—Plate 13, Van Dyke Red.

*Short needles.*—Quantity: on main stalks—few; on laterals—few.

I claim:

A new and distinct variety of rose plant characterized as to novelty by its vigorous growth and disease resistance and the peculiar color combination of its flowers, substantially as shown and described.

JEAN GAUJARD.